United States Patent [19]
Ohtaki et al.

[11] Patent Number: 5,861,085
[45] Date of Patent: Jan. 19, 1999

[54] METHOD OF PURIFYING 1,3-BIS(3-AMINOPROPYL)-1,1,3,3-TETRAORGANODISILOXANE

[75] Inventors: Hideaki Ohtaki; Hitoshi Koike, both of Tokyo, Japan

[73] Assignee: Yuki Gosei Kogyo Co., Ltd., Tokyo, Japan

[21] Appl. No.: 690,538

[22] Filed: Jul. 31, 1996

[30] Foreign Application Priority Data

Sep. 19, 1995 [JP] Japan ................................. 7-264912

[51] Int. Cl.$^6$ ......................................................... B01D 9/00

[52] U.S. Cl. ............................................................. 203/48

[58] Field of Search ................................................. 203/48

[56] References Cited

PUBLICATIONS

Siloxanmodifizierte Polypyromellitimide, Kuckertz, Die Makromolekulare Chemie 98 (1966), 1996.

Search Report, UK Patent Office, dated Nov. 5, 1996, 4 pages.

Chem. Abs. 66:2860 and Makromol. Chem., 98, 101–8 (1966), H. Kuckertz, "Siloxane–modified polypyromellitimides", 1 page.

*Primary Examiner*—Edward J. Cain
*Attorney, Agent, or Firm*—Faegre & Benson LLP

[57] ABSTRACT

A method of purifying 1,3-bis(3-aminopropyl)-1,1,3,3-tetraorganodisiloxane represented by the formula (I) as described hereinbefore, which comprises recrystallizing a crude product of the compound as its acid addition salt, and then neutralizing the acid addition salt to obtain a purified product of the compound. According to the method of the present invention, the compound of the formula (I) can be purified at high purity in high yield, and the purification treatment can be industrially conducted.

10 Claims, No Drawings

METHOD OF PURIFYING 1,3-BIS(3-AMINOPROPYL)-1,1,3,3-TETRAORGANODISILOXANE

BACKGROUND OF THE INVENTION

1. Field of the Invention

The present invention relates to a method of purifying 1,3-bis(3-aminopropyl)-1,1,3,3-tetraorganodisiloxane which is useful as a modifier for synthetic resins such as polyimides, polyamides or polyurethanes.

2. Prior Art

Conventionally, as a method of purifying 1,3-bis(3-amino-propyl)-1,1,3,3-tetraorganodisiloxane, a method of isolating crude 1,3-bis(3-aminopropyl)-1,1,3,3-tetraorganodisiloxane by distillation is known. However, this method involves the problem that, of impurities by-produced in a reaction for obtaining the desired product, impurities having a boiling point close to the boiling point of the desired product cannot be finally removed, and also Involves the problem that since the distillation is carried out while containing such impurities, thermal decomposition of the impurities occurs due to heat generated at the distillation, resulting in contamination of other impurities.

SUMMARY OF THE INVENTION

Accordingly, an object of the present invention is to provide a method that can purify 1,3-bis(3-aminopropyl)-1,1,3,3-tetraorganodisiloxane at high purity in high yield and industrially, i.e., in a large amount by simple procedures.

As a result of extensive study to attain the above object, it has been found that a high purity 1,3-bis(3-amino-propyl)-1,1,3,3-tetraorganodisiloxane can be obtained in high yield by recrystallizing crude 1,3-bis(3-aminopropyl)-1,1,3,3-tetraorganodisiloxane as its acid addition salt, and then neutralizing the acid addition salt.

The present invention relates to a method of purifying 1,3-bis(3-aminopropyl)-1,1,3,3-tetraorganodisiloxane represented by the following formula (I)

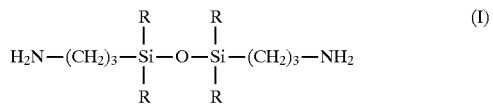

wherein each R may be the same or different is an alkyl group or an aryl group, which comprises recrystallizing a crude product of the above compound as its acid addition salt, and then neutralizing the acid addition salt to obtain a purified product of the compound.

DETAILED DESCRIPTION OF THE INVENTION 1,3-Bis(3-aminopropyl)-1,1,3,3-tetraorganodisiloxane used in the present invention is a compound represented by the formula (I) as described above. In the formula (I), R represents an alkyl group or an aryl group. Examples of the alkyl group include methyl, ethyl, propyl, butyl, pentyl, and cyclohexyl. Examples of the aryl group include phenyl, and tolyl. Of those, the alkyl group is preferred, and methyl is more preferred.

Examples of the compound represented by the above formula (I) include the following compounds:

1,3-bis(3-aminopropyl)-1,1,3,3-tetramethyldisiloxane;
1,3-bis(3-aminopropyl)-1,1,3,3-tetraethyldisiloxane;
1,3-bis(3-aminopropyl)-1,1,3,3-tetrapropyldisiloxane;
1,3-bis(3-aminopropyl)-1,1,3,3-tetrabutyldisiloxane;
1,3-bis(3-aminopropyl)-1,1,3,3-tetrapentyldisiloxane;
1,3-bis(3-aminopropyl)-1,1,3,3-tetracyclohexyldisiloxane;
1,3-bis(3-aminopropyl)-1,1,3,3-tetraphenyldisiloxane; and
1,3-bis(3-aminopropyl)-1,1,3,3-tetratolyldisiloxane.

According to the purification method of the present invention, crude 1,3-bis(3-aminopropyl)-1,1,3,3-tetraorgano-disiloxane is reacted with an acid in an appropriate solvent to form an acid addition salt of the compound. The acid used in this reaction is not particularly restricted so long as it crystallizes as an acid addition salt. Examples of the acid include hydrochloric acid, hydrobromic acid, sulfuric acid, and nitric acid. Of those acids, hydrochloric acid is preferred.

The amount of the acid used is at least two times the equivalent of 1,3-bis(3-aminopropyl)-1,1,3,3-tetraorganodisiloxane.

The reaction temperature for the formation of the acid addition salt is generally from 15° to 30° C., i.e., room temperature. The reaction completes instantaneously.

Examples of the solvent used in the formation of the acid addition salt include water, alcohols such as methanol, ethanol or isopropanol, hydrocarbons such as hexane or toluene, ethers such as ethyl ether, and halogenated hydrocarbons such as dichloromethane. Of those, alcohols are preferred and more particularly isopropanol is preferred.

Recrystallization of the acid addition salt is then conducted. A solvent used in this recrystallization is not particularly restricted, but the same solvent as used in the formation of the acid addition salt is preferred for its simple operation.

The recrystallized acid addition salt is neutralized with an alkali, thereby high purity 1,3-bis(3-aminopropyl)-1,1,3,3-tetraorganodisiloxane is obtained in high yield. Examples of the alkali used in this neutralization include sodium hydroxide, potassium hydroxide, and sodium carbonate. Of those, sodium hydroxide is preferred. The amount of the alkali used is the equivalent or more based on the amount of the acid in the acid addition salt.

The temperature of the neutralization reaction is room temperature, and the reaction is generally completed within 1 hour. As described above, according to the method of the present invention, 1,3-bis(3-aminopropyl)-1,1,3,3-tetraorganodisiloxane which is useful as a modifier for synthetic resins can be industrially purified at high purity in high yield.

EXAMPLES

The present invention is described in more detail with reference to the following examples, but it should be understood that the invention is not limited by those examples.

Example 1

(1) Formation of acid addition salt of 1,3-bis(3-aminopropyl)-1,1,3,3-tetramethyldisiloxane and recrystallization step (Run 1):

In a 500 ml four-necked flask equipped with a stirrer, a thermometer, a condenser, and a dropping funnel was placed 24.9 g (0.1 mole) of 1,3-bis(3-aminopropyl)-1,1,3,3-tetramethyldisiloxane having a gas chromatography purity of 98.4%. 31.3 g (0.3 mole) of concentrated hydrochloric acid was dropwise added to the flask, and the resulting mixture was stirred at room temperature for 30 minutes. 300 g of isopropanol was added to the solution. The resulting mixture was heated under reduced pressure, and isopropanol was distilled off while conducting azeotropic distillation, to obtain a concentrated and dried product. The concentrated and dried product thus obtained was recrystallized from isopropanol to obtain 28.9 g (yield: 90%) of 1,3-bis(3-amino-propyl)-1,1,3,3-tetramethyldisiloxane dihydrochloride which is an acid addition salt.

(2) Formation of acid addition salt of 1,3-bis(3-aminopropyl)-1,1,3,3-tetramethyldisiloxane and recrystallization step (Run 2):

In a 5 liters four-necked flask equipped with a stirrer, a thermometer, a gas-inlet tube, and a condenser were placed 1000 g (4.0 moles) of 1,3-bis(3-aminopropyl)-1,1,3,3-tetramethyldisiloxane having a gas chromatography purity of 98.4%, and 2,600 g of isopropanol. 360 g (9.9 moles) of hydrogen chloride gas was bubbled into the solution while stirring the mixture at room temperature. Recrystallization was conducted to obtain 1,250 g (yield: 97%) of 1,3-bis(3-aminopropyl)-1,1,3,3-tetramethyldisiloxane dihydrochloride which was an acid addition salt.

(3) Neutralization of acid addition salt and separation step:

In a 5 liters four-necked flask equipped with a stirrer, a thermometer, and a condenser was placed 1,250 g (3.9 moles) of 1,3-bis(3-aminopropyl)-1,1,3,3-tetramethyldisiloxane dihydrochloride obtained in (1) or (2) above. 400 g of water was added to the flask to dissolve the dihydrochloride addition salt. 1,040 g (7.8 moles) of a 30% sodium hydroxide aqueous solution and 2,500 g of toluene were then added to the solution, and the resulting mixture was stirred at room temperature for 1 hour. An organic layer was concentrated, followed by distillation under reduced pressure, to obtain 777 g (yield: 80%) of 1,3-bis(3-aminopropyl)-1,1,3,3-tetra-methyldisiloxane as a fraction having a boiling point of 112°–114° C./1.0 Torr. As a result of a gas chromatography analysis, the purity of the product was 99.9%.

The present invention is described in the above example with reference to the purification of 1,3-bis(3-aminopropyl)-1,1,3,3-tetramethyldisiloxane, but purification of other 1,3-bis(3-aminopropyl)-1,1,3,3-tetraorganodisiloxanes can be conducted in the same manner as described above, and purified products can similarly be obtained at high purity in high yield.

What is claimed is:

1. A method of purifying 1,3-bis(3-aminopropyl)-1,1,3,3-tetraorganodisiloxane represented by the following formula (I):

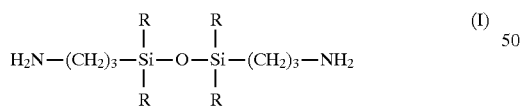

wherein each R may be the same or different and represents an alkyl group or an aryl group, which method comprises the steps of
   (a) reacting the compound according to formula (I) with hydrochloric acid to form a hydrochloric acid addition salt of the compound according to formula (I);
   (b) recrystallizing the hydrochloric acid addition salt from a first admixture containing isopropanol;
   (c) neutralizing the hydrochloric acid addition salt by combining the hydrochloric acid addition salt with aqueous sodium hydroxide and toluene to provide a second admixture comprising an organic layer comprising toluene and the compound according to formula (I); and
   (d) obtaining the compound according to formula (I) from the organic layer of the second admixture.

2. The method as claimed in claim 1, wherein R in the formula (I) is methyl group.

3. A method of purifying 1,3-bis(3-aminopropyl)-1,1,3,3-tetraorganodisiloxane represented by the following formula (II):

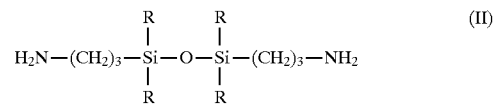

wherein each R may be the same or different and represents an alkyl group or an aryl group, which method comprises the steps of:
   (a) reacting the compound according to formula (II) with an acid to form an acid addition salt of the compound according to formula (II);
   (b) recrystallizing the acid addition salt;
   (c) neutralizing the acid addition salt by combining the acid addition salt with an aqueous base and an organic solvent to provide an admixture comprising an organic layer comprising the organic solvent and the compound according to formula (II); and
   (d) obtaining the compound according to formula (II) from the organic layer of the admixture.

4. The method of claim 3, wherein each R is a methyl group.

5. The method of claim 3, wherein the acid is hydrochloric acid.

6. The method of claim 3, wherein the recrystallization step comprises:
   (a) adding isopropanol to the acid addition salt; and
   (b) removing the isopropanol to provide a recrystallized acid addition salt of the compound according to formula (II).

7. The method of claim 3, wherein the organic solvent is toluene.

8. The method of claim 3, wherein the aqueous base is sodium hydroxide.

9. A method of purifying 1,3-bis(3-aminopropyl)-1,1,1,3,3-tetraorganodisiloxane represented by the following formula (III):

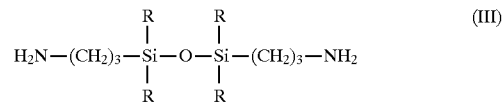

wherein each R may be the same or different and represents an alkyl group or an aryl group, which method comprises the steps of:
   (a) reacting the compound according to formula (III) with an acid to form an acid addition salt of the compound according to formula (III);
   (b) recrystallizing the acid addition salt from a first admixture containing isopropanol;
   (c) neutralizing the acid addition salt by combining the acid addition salt with an aqueous base and an organic solvent to provide a second admixture comprising an organic layer comprising the organic solvent and the compound according to formula (III); and
   (d) obtaining the compound according to formula (III) from the organic layer of the second admixture.

10. A method of purifying 1,3-bis(3-aminopropyl)-1,1,3,3-tetraorganodisiloxane represented by the following formula (IV):

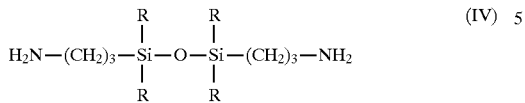
(IV)

wherein each R may be the same or different and represents an alkyl group or an aryl group, which method comprises the steps of:

(a) adding isopropanol to the compound according to formula (IV) to provide a first admixture;

(b) combining the first admixture with an acid to form an acid addition salt of the compound according to formula (IV);

(c) removing the isopropanol to provide a recrystallized acid addition salt of the compound according to formula (IV)

(d) neutralizing the acid addition salt by combining the acid addition salt with an aqueous base and an organic solvent to provide a second admixture comprising an organic layer comprising the organic solvent and the compound according to formula (IV); and (e) obtaining the compound according to formula (IV) from the organic layer of the second admixture.

* * * * *